US008313932B2

(12) United States Patent
Moser et al.

(10) Patent No.: US 8,313,932 B2
(45) Date of Patent: Nov. 20, 2012

(54) POLYMERASE INHIBITOR AND METHOD OF USING SAME

(75) Inventors: Michael James Moser, Madison, WI (US); David J. Marshall, Madison, WI (US); James R. Prudent, Madison, WI (US); Cristopher V. Van Hout, Ann Arbor, MI (US); Christine A. Larsen, Corvallis, OR (US)

(73) Assignee: Luminex Corporation, Austin, TX (US)

( * ) Notice: Subject to any disclaimer, the term of this patent is extended or adjusted under 35 U.S.C. 154(b) by 92 days.

(21) Appl. No.: 12/884,575

(22) Filed: Sep. 17, 2010

(65) Prior Publication Data

US 2011/0104678 A1 May 5, 2011

Related U.S. Application Data

(62) Division of application No. 10/551,705, filed as application No. PCT/US2004/010029 on Apr. 1, 2004, now Pat. No. 7,820,808.

(60) Provisional application No. 60/459,672, filed on Apr. 1, 2003.

(51) Int. Cl.
*C12P 19/34* (2006.01)
*A61K 48/00* (2006.01)
*C07H 21/04* (2006.01)

(52) U.S. Cl. ................ 435/91.2; 536/23.1; 536/24.5; 514/44

(58) Field of Classification Search ................ None
See application file for complete search history.

(56) References Cited

U.S. PATENT DOCUMENTS

| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 4,996,143 A | 2/1991 | Heller et al. |
| 5,126,439 A | 6/1992 | Rappaport |
| 5,177,064 A | 1/1993 | Bodor |
| 5,210,015 A | 5/1993 | Gelfand et al. |
| 5,412,088 A | 5/1995 | Jones et al. |
| 5,432,272 A | 7/1995 | Benner |
| 5,470,974 A | 11/1995 | Summerton et al. |
| 5,604,097 A | 2/1997 | Brenner |
| 5,605,794 A | 2/1997 | Rust et al. |
| 5,679,524 A | 10/1997 | Nikiforov et al. |
| 5,681,702 A | 10/1997 | Collins et al. |
| 5,705,621 A | 1/1998 | Ravikumar |
| 5,736,330 A | 4/1998 | Fulton |
| 5,843,669 A | 12/1998 | Kaiser et al. |
| 5,846,717 A | 12/1998 | Brow et al. |
| 5,856,092 A | 1/1999 | Dale et al. |
| 5,928,869 A | 7/1999 | Nadeau et al. |
| 5,958,784 A | 9/1999 | Benner |
| 5,965,364 A | 10/1999 | Benner |
| 6,001,983 A | 12/1999 | Benner |
| 6,007,984 A | 12/1999 | Wang et al. |
| 6,037,120 A | 3/2000 | Benner |
| 6,046,807 A | 4/2000 | Chandler |
| 6,054,270 A | 4/2000 | Southern |
| 6,057,107 A | 5/2000 | Fulton |
| 6,140,496 A | 10/2000 | Benner |
| 6,200,757 B1 | 3/2001 | Kurn et al. |
| 6,232,462 B1 | 5/2001 | Collins et al. |
| 6,287,766 B1 | 9/2001 | Nolan et al. |
| 6,294,336 B1 | 9/2001 | Boyce-Jacino et al. |
| 6,444,798 B1 | 9/2002 | Benner |
| 6,509,157 B1 | 1/2003 | Martinez |
| 6,548,250 B1 | 4/2003 | Sorge |
| 6,617,106 B1 | 9/2003 | Benner |
| 6,627,456 B1 | 9/2003 | Benner |
| 6,833,257 B2 | 12/2004 | Lee et al. |
| 6,977,161 B2 | 12/2005 | Grenier et al. |
| 2002/0055104 A1 | 5/2002 | Michelotti |
| 2002/0132221 A1 | 9/2002 | Chee et al. |
| 2002/0150900 A1 | 10/2002 | Marshall et al. |
| 2003/0194705 A1 | 10/2003 | Schroth |
| 2004/0106108 A1 | 6/2004 | Grenier et al. |
| 2005/0014163 A1 | 1/2005 | Dong et al. |
| 2005/0084894 A1 | 4/2005 | Brow et al. |
| 2006/0078936 A1 | 4/2006 | Grenier et al. |

FOREIGN PATENT DOCUMENTS

| EP | 0 382 433 | 8/1990 |
| EP | 0 416 817 | 3/1991 |
| EP | 0 742 287 | 11/1996 |
| EP | 0 915 174 | 5/1999 |
| JP | 64-034300 | 2/1989 |
| JP | 09-511149 | 11/1997 |
| WO | WO-90/06042 | 6/1990 |
| WO | WO-92/11389 | 7/1992 |
| WO | WO-94/21820 | 9/1994 |
| WO | WO-96/31622 | 10/1996 |
| WO | WO-97/46711 | 11/1997 |
| WO | WO-98/14610 | 4/1998 |
| WO | WO-00/52207 | 9/2000 |
| WO | WO-01/75139 | 10/2001 |
| WO | WO-01/90417 | 11/2001 |
| WO | WO-03/046149 | 6/2003 |

OTHER PUBLICATIONS

Australian Examiner's Report for Patent Application No. 2004227353 dated Sep. 24, 2009.

(Continued)

*Primary Examiner* — Amy Bowman
(74) *Attorney, Agent, or Firm* — Fulbright & Jaworski L.L.P.

(57) ABSTRACT

The present invention provides nucleic acid based polymerase inhibitors and methods for reducing non-specific polymerase extension and amplification in nucleic acid amplification reactions. The polymerase inhibitors provide a double stranded nucleic acid portion that is recognized by a polymerase enzyme as a template for extension but is incapable of being extended by the polymerase enzyme. The polymerase binds to the polymerase inhibitor which sequesters the enzyme until the temperature achieves a level that denatures the double stranded portion of the inhibitor after which the polymerase is released and can then catalyze nucleic acid extension.

15 Claims, 10 Drawing Sheets

OTHER PUBLICATIONS

Biggins et al., "A continuous assay for DNA cleavage: The application of "break lights" to enediynes, iron-dependent agents, and nucleases", PNAS, vol. 97, No. 25, Dec. 5, 2000 (pp. 13537-13542).

Chung et al., "Biochemical Studies on Capped RNA Primers Identify a Class of Oligonucleotide Inhibitors of the Influenza Virus RNA Polymerase," 1994, 91(6), pp. 2372-2376.

Cobianchi et al., "Enzymes for Modifying and Labeling DNA and RNA," Methods in Enzymology, vol. 152, Copyright © 1987 by Academic Press, Inc., (pp. 94-110).

Diatchenko, L. et al., "Suppression subtractive hybridization: a method for generating differentially regulated or tissue-specific cDNA probes and libraries," Proc. Natl. Acad. Sci. USA, Jun. 11, 1996, vol. 93, No. 12, pp. 6025-6030.

First Communication received in European Appln. No. 04758726.6 dated May 29, 2009.

Hall et al., "Sensitive detection of DNA polymorphisms by the serial invasive signal amplification reaction", PNAS, vol. 97, No. 15, Jul. 18, 2000 (pp. 8272-8277).

Horlacher et al., "Recognition by viral and cellular DNA polymerases of nucleosides bearing bases with nonstandard hydrogen bonding patterns", Proc. Natl. Acad. Sci., vol. 92, Jul. 1995 (pp. 6329-6333).

Japanese Office Action received for JP Appln. No. 2006-509580 dated Feb. 25, 2010.

Johnson et al., "A third base pair for the polymerase chain reaction: inserting isoC and isoG", Nucleic Acids Research, vol. 32, No. 6, 2004, (pp. 1937-1941).

Jurczyk et al., "Synthesis of 2'-Deoxyisoguanosine 5'-Triphosphate and 2'-Deoxy-5-methylisocytidine 5'-Triphosphate", Helvetica Chimica Acta, vol. 82, 1999 (pp. 1005-1015).

Kaboev, O. et al., "PCR hot start using primers with the structure of molecular beacons (hairpin-like structures)," Nucleic Acids Research, Oxford University Press, Surrey, GB, vol. 28, No. 21, Nov. 1, 2000, p. E94.

Kainz. P. et al., "Specificity-enhanced hot-start PCR: Addition of double-stranded DNA fragments adapted to the annealing temperature," Biotechniques, Informa Life Sciences Publishing, Westborough, MA, US, vol. 28, No. 2, pp. 278-282, Feb. 1, 2000.

Lutz, Michael J. et al., "Differential discrimination of DNA polymerases for variants of the non-standard nucleobase pair between xanthosine and 2,4-diaminopyrimidine, two components of an expanded genetic alphabet", Nucleic Acids Research, vol. 24, No. 7, 1996 (pp. 1308-1313).

Lutz, Stefan et al., "An in vitro screening technique for DNA polymerases that can incorporate modified nucleotides. Pseudothymidine as a substrate for thermostable polymerases", Nucleic Acids Research, vol. 27, No. 13, 1999 (pp. 2792-2798).

Moser et al., "Enzymatic repair of an expanded genetic information system", Nucleic Acids Research, vol. 31, No. 27, 2003 (pp. 5048-5053).

Moser et al., "Quantifying Mixed Populations of Drug-Resistant Human Immunodeficiency Virus type 1", Antimicrobial Agents and Chemotherapy, vol. 49, No. 8, Aug. 2005 (pp. 3334-3340).

Newton et al., "The production of PCR products with 5' single-stranded tails using primers that incorporate novel phosphoramidite intermediates", Nucleic Acids Research, vol. 21, No. 5, 1993 (pp. 1155-1162).

Non-final Office Action received for U.S. Appl. No. 10/551,705 dated Jan. 26, 2010.

Notice of Allowance received for U.S. Appl. No. 10/551,705 dated Jun. 28, 2010.

PCT International Search Report based on International Application No. PCT/US04/10029, date of mailing of the International Search Report Apr. 5, 2005.

PCT Written Opinion based on International Application No. PCT/US04/10029, date of mailing Apr. 5, 2005.

Piccirilli et al., "Enzymatic incorporation of a new base pair into DNA and RNA extends the genetic alphabet", Reprinted from Nature, vol. 343, No. 6253, Jan. 4, 1990 (pp. 33-37).

Randerath et al., "3H and 32P Derivative Methods for Base Composition and Sequence Analysis of RNA", Methods in Enzymology, vol. 65, Copyright © 1980 by Academic Press, Inc., (pp. 638-681).

Sepiol et al., "Tautomerism of Isoguanosine and Solvent-Induced Keto-Enol Equilibrium", Z. Naturforsch, 1976 (pp. 361-370).

Siebert, P. et al., "An improved PCR method for walking in unclonedgenomic DNA," Nucl. Acids Res. 1995 23: 1087-1088.

Sismour et al., "PCR amplification of DNA containing non-standard base pairs by variants of reverse transcriptase from Human Immunodeficiency Virus-1", Nucleic Acids Research, vol. 32, No. 2, 2004 (pp. 728-735).

Sismour et al., "The use of thymidine analogs to improve the replication of an extra DNA base pair: a synthetic biological system", Nucleic Acids Research, vol. 33, No. 17, 2005 (pp. 5640-5646).

Supplementary European Search Report for European Patent Application No. 04 75 8726 dated Feb. 16, 2009.

Switzer et al., "Enzymatic Recognition of the Base Pair between Isocytidine and Isoguanosine", Biochemistry, vol. 32, No. 39, 1993 (pp. 10489-10496).

Tabrizi et al., "Evaluation of real time polymerase chain reaction assays for confirmation of *Neisseria gonorrhoeae* in clinical samples tested positive in the Roche Cobas Amplicor assay", Sex Transm Infect, vol. 80, 2004 (pp. 68-71).

Tor et al., "Site-Specific Enzymatic Incorporation of an Unnatural Base, N6-(6-Aminohexyl)isoguanosine, into RNA", J. Am. Chem. Soc., vol. 115, No. 11, 1993 (pp. 4461-4467).

Von Krosigk et al., "pH-Independent Triple Helix Formation by an Oligonucleotide Containing a Pyrazine Donor-Donor-Acceptor Base", J. Am. Chem. Soc., vol. 117, No. 19, 1995 (pp. 5361-5362).

Walker et al., "Isothermal in vitro amplification of DNA by a restriction enzyme/DNA polymerase system", Proc. Natl. Acad. Sci., vol. 89, Jan. 1992 (pp. 392-396).

Watanabe et al., "Two-Step Synthesis of 2,5'-Anhydronucleosides From Thymidine, 2'-Deoxyuridine, and 2'-Deoxy-5-fluorouridine", Nucleic Acid Chemistry (pp. 273-277).

Zubay, "A Case for an Additional RNA Base Pair in Early Evolution", Reprint from: The Roots of Modern Biochemistry, © 1988 Walter de Gruyter & Co., Berlin, New York (4 pp.).

Office Communication, issued in European Patent Application 04 758 726.6, mailed on Jan. 18, 2012.

Office Action received in Canadian Appln. No. 2,521,127 dated Jan. 11, 2011.

```
                    T
           ddCAGTC  T
GCTGTCTGGTCCGTCAG  T
                   T

DM429 GCTGTCTGGTCCGTCAGTTTTCTGACdd
dG = -2.85 dH = -43.5 dS = -131.2 Tm = 58.3 ddCGCAGTGC  T
GCTGTCTGGTCCGCCGTCACG  T
                       T

MM166 GCTGTCTGGTCGCGCCGTCACGTTTTCGTGACGdd
dG = -9.02 dH = -75.1 dS = -213.1 Tm = 79.2 ddCAATAATA  T
GCTGTCTGGTCCGTTATTAT  T
                     T

DM432 GCTGTCTGGTCCGTTATTATTTTATAATAACdd
dG = -2.57 dH = -59.8 dS = -184.4 Tm = 51.1 ddCAATAATG  T
GCTGTCTGGTCCGTTATTAC  T
                     T

DM433 GCTGTCTGGTCCGTTATTACTTTTGTAATAACdd
dG = -3.73 dH = -64.0 dS = -194.4 Tm = 56.8
```

```
                    T
           ddCAGTAC  T
GCTGTCTGGTCCGTCATG  T
                    T

DM430 GCTGTCTGGTCCGTCATGTTTTCATGACdd
dG = -3.71 dH = -51.4 dS = -153.8 Tm = 61.1 ddCAGTAT  T
GCTGTCTGGTCCGTCATA  T
                    T

DM431 GCTGTCTGGTCCGTCATATTTTATGACdd
dG = -2.34 dH = -46.4 dS = -142.2 Tm = 53.2 ddCAATAATATA  T
GCTGTCTGGTCCGTTATATTT  T
                       T

DM434 GCTGTCTGGTCCGTTATATTTTTATATAATAACdd
dG = -3.65 dH = -74.2 dS = -227.3 Tm = 53.3 ddCAATAATATG  T
GCTGTCTGGTCCGTTATTATAC  T
                        T

DM435 GCTGTCTGGTCCGTTATTATACTTTTGTATAATAACdd
dG = -4.81 dH = -78.4 dS = -237.3 Tm = 57.2
```

```
                              T
          GCTGAGCTGC  T
5' FAM-TXAGAGTCTGGTGCCGACTCGACG  T
                              T

DM436 FAM-TXAGAGTCTGGTGCCGACTCGACGTTTCGTCGAGTCG
```

FIG. 1A

```
MM001  CACGACAGGAGCAGACAGGAXYGCTCACGTTTTCGTGAGCT      ΔG° = -9.0 kcal/mole at 37 °C
MM119  CACACAGGAGCAXXAGCTCACGTTTTCGTGAGCT             ΔH° = -75.1 kcal/mole
                                                     ΔS° = -213.1 cal/(°K mol)
                                                     Tm = 79.2 °C assuming 2 state model DM362  GCTGTCTGGTXXGCTCACGTTTTCGTGAGC
DM363  GCTGTCTGGTXXCGCTCACGTTTTCGTGAGCG                        T
DM364  GCTGTCTGGTCCCGCTCACGTTTTCGTGAGCGTT              ddCGCAGTGC T
DM365  GCTGTCTGGTXXCGACTCGACGTTTTCGTGAGTCG            GCTGTCTGGTCCGCGTCACG T
DM366  GCTGTCTGGTCCGGACTCGACGTTTTCGTCGAG[U-ome][C-ome][ddC]            T
                                                     GCTGTCTGGTCCGCGTCACGTTTTCGTGACG-ddC T     T
             CGAGTGC  T                              G° = -7.52 kcal/mole at 37°C
5' CACGACAGGCAGACAGGAXYGCTCACG T                     H° = -69.0 kcal/mole
                               T                     S° = -198.3 cal/(°K mol)
                                                     Tm = 74.8°C assuming a 2 state model

T
5' CACGACAGCCAGACAGGAGCAXYGCTCACGTTTTCGTGAGCT  MM001

8    T
        TCGAGTGC   T                                 G° = -8.00 kcal/mole at 37°C
5' CACACAGGAGCAXXAGCTCACG  T                         H° = -65.5 kcal/mole
                           T                         S° = -185.2 cal/(°K mol)
                                                     Tm = 80.2°C assuming a 2 state model

5' CACACAGGAGCAXXAGCTCACGTTTTCGTGAGCT  MM119

8     T
       CGAGTGC  T                                    G° = -6.9 kcal/mole at 37°C
5' GCTGTCTGGTXXGCTCACG  T                            H° = -63.9 kcal/mole
                        T                            S° = -183.8 cal/(°K mol)
                                                     Tm = 74.5°C assuming a 2 state model

5' GCTGTCTGGTXXGCTCACGTTTTCGTGAGC  DM362

8      T
       GCGAGTGC   T                                  G° = -9.0 kcal/mole at 37°C
5' GCTGTCTGGTXXCGCTCACG  T                           H° = -74.9 kcal/mole
                         T                           S° = -212.5 cal/(°K mol)
                                                     Tm = 79.4°C assuming a 2 state model

5' GCTGTCTGGTXXCGCTCACGTTTTCGTGAGCG  DM363

TT   8   T
       GCGAGTGC  T                                   G° = -9.3 kcal/mole at 37°C
5' GCTGTCTGGTCCCGCTCACG  T                           H° = -79.3 kcal/mole
                         T                           S° = -225.7 cal/(°K mol)
                                                     Tm = 78.2°C assuming a 2 state model

5' GCTGTCTGGTCCCGCTCACGTTTTCGTGAGCGTT  DM364

10   T
        GCTGAGCTGC  T                                G° = -11.2 kcal/mole at 37°C
5' GCTGTCTGGTXXCGACTCGACG  T                         H° = -92.0 kcal/mole
                           T                         S° = -260.5 cal/(°K mol)
                                                     Tm = 80°C assuming a 2 state model

5' GCTGTCTGGTXXCGACTCGACGTTTTCGTCGAGTCG  DM365

10    T
        CCTGAGCTGC  T                                G° = -10.7 kcal/mole at 37°C
5' GCTGTCTGGTCCGGACTCGACG  T                         H° = -89.0 kcal/mole
                           T                         S° = -252.5 cal/(°K mol)
                                                     Tm = 79.4°C assuming a 2 state model 5' GCTGTCTGGTCCGGACTCGACGTTTTCGTCGAG[Uome][Come][ddC]  DM366
```

```
5'   GCTGTCTCTGGTCCGTTATTATAC-PO4              MM308  (o-methyl)
5'   GCTGTCTCTGGTCCGTTATTATAC-PO4              MM309
5'   GCTGTCTCTGGTCCGTTATTATACdd                MM317
5'   GCTGTCTCTGGTCCGTTATTATAC-Biotin           CL085
          3'  ddCCAGGCAATAATATG                MM312  Tm=45°
          3'  ddCAGGCAATAATATG                 MM311  Tm=40.5°
          3'     ddCAATAATATG                  MM310  Tm=24.3°
          3'  ddCAGGCAATAATATGGTCTGTCG         SCJ091
          3'  ddCCAGGCAATAATATGGTCTGTCG        MM338

5'-GCTGTYTGGTGXGTTAYTATAC-Biotin               CL077
5'-GCTGTYTGGTGXGTTAYTATAC-PO4                  CL062
          ddCYCAATXATATG-5'                    CL063
          ddCACYCAATXATATG-5'                  CL064/CL078  Tm=50.4
          ddCCACYCAATXATATG-5'                 CL065/CL079  Tm=55

5'-GCTGTYTGGTAXGTTAYTATAC-PO4                  CL091/CL100
          ddCATYCAATXATATG-5'                  CL092/CL101
```

FIG. 2 are duplex decoys

FIG. 3
A) 
B) 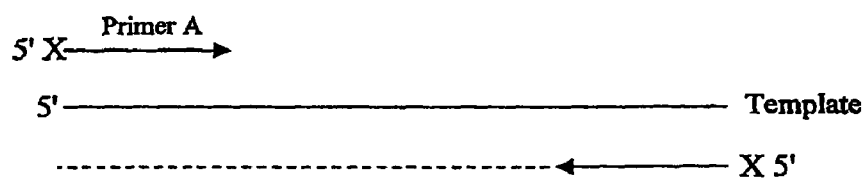
C) 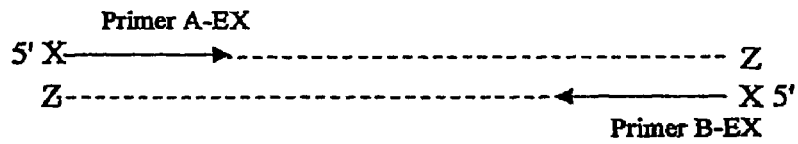
D) 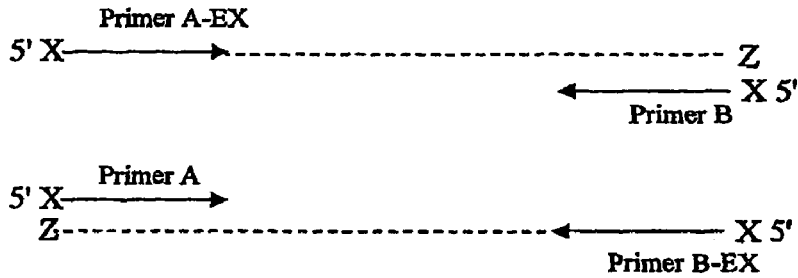

FIG. 4
A)
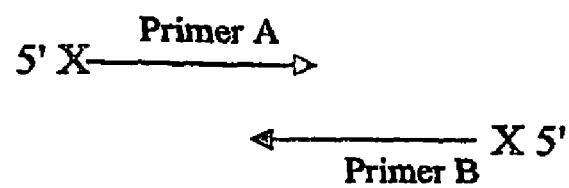
B)
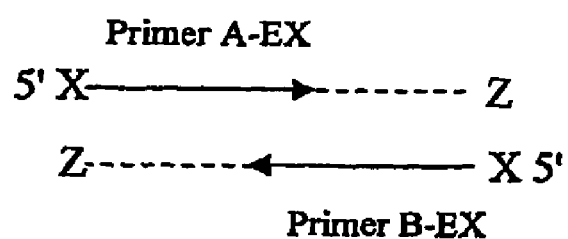

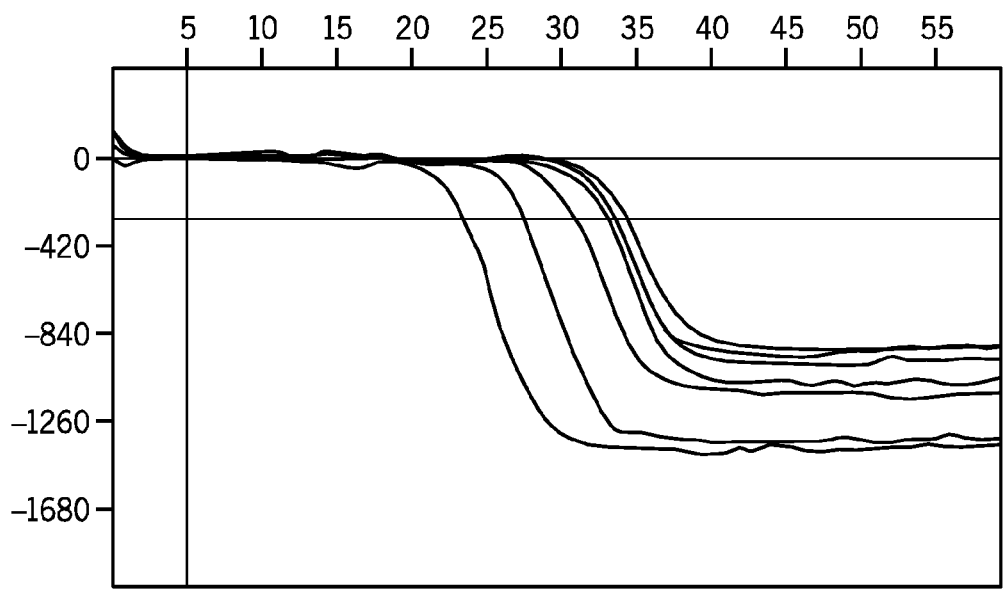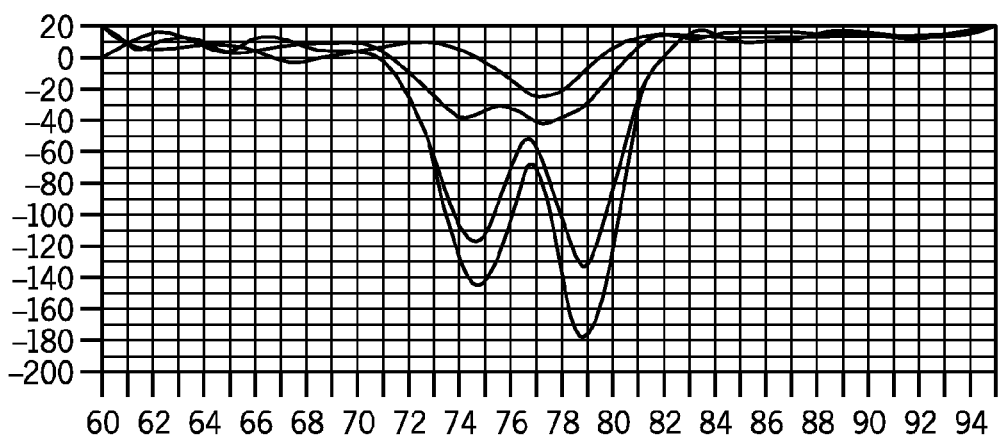
FIG. 5A

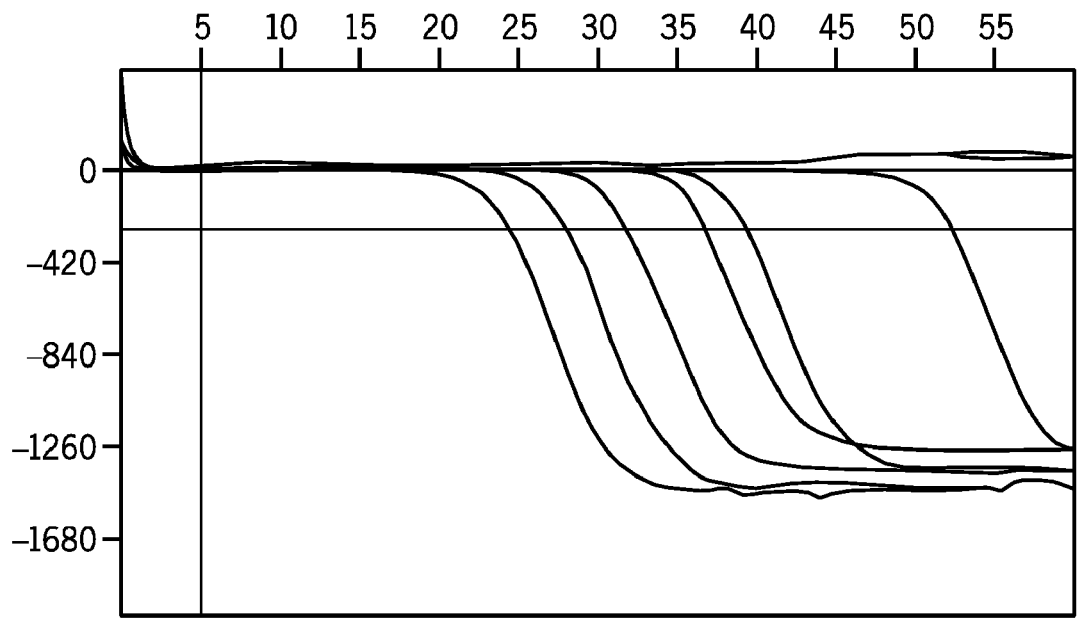
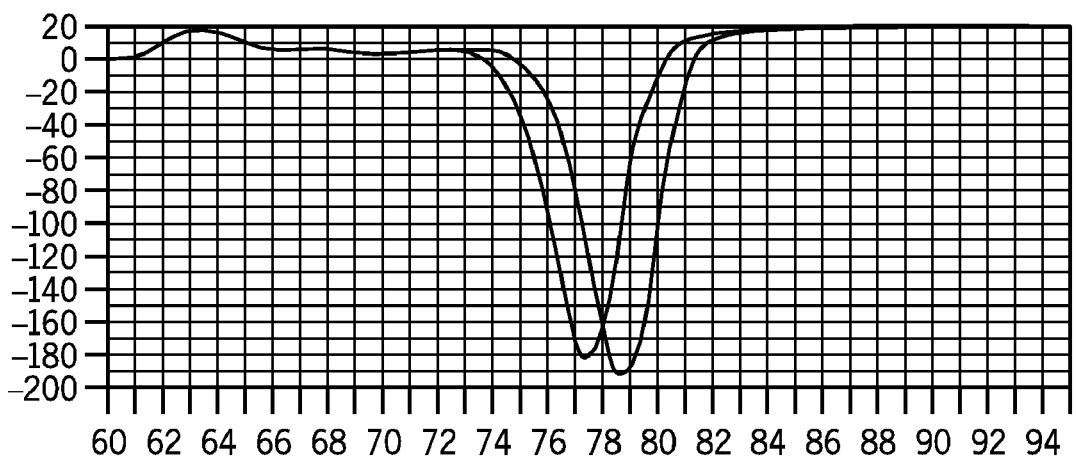
FIG. 5C

POLYMERASE INHIBITOR AND METHOD OF USING SAME

CROSS-REFERENCE TO RELATED PATENT APPLICATIONS

This application is a Divisional of U.S. application Ser. No. 10/551,705, filed Jul. 14, 2006, which is a National Stage Entry of PCT/US04/10029, filed Apr. 1, 2004, which claims priority to U.S. Provisional Application No. 60/459,672, filed Apr. 1, 2003, the entire contents of all of which are incorporated herein by reference in its entirety.

FIELD OF INVENTION

The present invention relates to methods and reagents that inhibit nucleic acid polymerase activity. More specifically, the present invention relates to methods and nucleic acids that prevent non-specific nucleic acid extension or amplification by nucleic acid polymerases at low temperatures.

BACKGROUND OF THE INVENTION

The Polymerase Chain Reaction (PCR) has proven to be a versatile and powerful technique for amplifying nucleic acids. The PCR utilizes the ability of natural or recombinant DNA polymerases to reproduce a target nucleic acid to high levels. Theoretically, this procedure is capable of producing logarithmic reproductions, (amplification) of a single copy of DNA. However, the sensitivity of the PCR process is compromised by a number of factors during the amplification process, resulting in a significant loss of sensitivity. One of the major problems is the development of a non-specific product during the reaction, commonly known as "primer-dimers". When these products form, they result in the removal of both primers and deoxyribonucleoside triphosphates (dNTPs) from the reaction, thereby reducing the level of amplification of the desired target and concurrently reducing sensitivity of the reaction.

In order to avoid these deficiencies, the "hot start" PCR technique was developed. A hot start reaction involves preventing the PCR reaction from occurring at lower, non-specific temperatures before temperature cycling is initiated and amplification ensues. Hot-start reaction techniques have been based on inactivation of the polymerase at the lower temperature, or alternatively withholding a critical component of the PCR reaction, such as polymerase, nucleoside triphosphates, or $Mg^{2+}$.

In the initial hot start technique the reaction mixture was heated above the annealing Tm of the primers prior to addition of a critical component of the reaction. However, this method is cumbersome, prone to contamination and is not amenable to high throughput application since multiple additions must be performed. It also involves the use of a mineral oil overlay since addition of reagents to reaction must be performed at elevated temperatures. Additionally, once reaction begins dimer inhibition no longer occurs.

A similar method to the one described above is the wax barrier method where mineral oil is replaced with a wax that liquefies at high temperatures, described in Chou et al., *Nucleic Acids Res* 20 (7), p. 1717 (1992). The reaction mixture is heated and cooled prior to addition of a critical component of the reaction causing the wax to harden forming a barrier. A limiting component is added on top of the wax above reaction mix, and when temperature cycling is initiated, the wax melts allowing the denser aqueous limiting reagent to sink through the liquid wax forming complete reaction mixture and amplification ensues. Unfortunately, this technique requires cumbersome heating-cooling-addition of limiting reagent. Additionally, wax must be added to each well as a solid pellet and thus the method is very low throughput and cannot be automated. Certain waxes have higher degrees of opacity so the use of fluorescence detection for real-time PCR can be limited.

Another hot start technique involves conjugating the polymerase with an antibody (Ab) or mixture of antibodies directed against the polymerase protein as described in U.S. Pat. No. 5,338,671. The Ab inactivates the polymerase at low temperatures and when the reaction is heated the Ab is irreversibly inactivated due to denaturation. Ab inactivation allows polymerase to become active during subsequent annealing and extension steps allowing PCR to occur. This technique is also subject to several limitations including the fact that the Ab is expensive and is specific only to a single polymerase. Thus, a new Ab must be isolated to react with each type of polymerase. This methodology also cannot be used with reverse transcriptase (RT) because elevated temperature sufficient to inactivate the Ab also inactivates the RT.

Another method involves chemical modification of polymerase enzyme with a chemical moiety such as a cyclic anhydride that attaches to lysine as disclosed in U.S. Pat. No. 6,183,998. Derivatization inactivates the polymerase which when incubated at an elevated temperature in the presence of a temperature-sensitive buffer, such as Tris, results in a significant pH decrease at 95° C. The acid conditions resulting at this elevated temperature reverse the chemical derivitization and activates the enzyme. The drawback of this technique includes the requirement of long-term incubation, generally greater than 10 minutes at denaturing temperature. Acid sensitive fluorophore detection chemistries can be adversely affected by the resulting pH changes. This methodology also cannot be used with RT because elevated temperature sufficient to inactivate the anhydride also inactivates RT. Moreover, reversal of chemical derivative is not efficient and the full activity of enzyme is not recovered necessitating increasing enzyme concentrations for many applications.

One hot start method that sequesters magnesium involves the addition of phosphoric acid to buffer causing room temperature precipitation of magnesium ions that are required for PCR. See, Barnes et al., *Mol Cell Probes* 16 (3), p. 167 (2002) and U.S. Pat. No. 6,403,341. Incubation of the reaction mixture at 95° C. resolubilizes the magnesium precipitate and magnesium ions will stay in solution at elevated reaction temperatures of PCR. In that method, efficient precipitation of the magnesium ion is dependent on the use of a special buffer. Also inhibition of PCR may not be complete because not all of the magnesium ion precipitates. As above, acid conditions may adversely affect sensitive fluorophores or other moieties such as isobases and this methodology also cannot be used with RT because elevated temperature sufficient to inactivate the anhydride also inactivates the RT Still another hot start technique is based on the use aptamers, polypeptides or single-stranded nucleic acids that are selected to be specific for a particular polymerase. The aptamer method involves selection and amplification of structured nucleic acids, using the SELEX technique, that specifically bind to and inhibit the polymerase. These techniques are described in U.S. Pat. Nos. 5,693,502, 5,763,173, 5,874,557, 6,020,130, and 6,183,967 and Dang et al. *J Mol Biol* 264 (2), p. 268 (1996). Selection is done at low temperatures and incubation of the aptamer at elevated temperatures denatures the structural elements required for specific inhibition. Denatured aptamer can no longer inhibit polymerase activity allowing PCR. However, the aptamer is specific only to a single polymerase or closely related polymerases. Thus, a new aptamer is required to react with each type or family of polymerase. Also temperature optima of aptamers may not be easily predicted or controlled and inhibitory activity of the aptamer may not be fully reversed at a given temperature necessitating precise optimization of aptamer/enzyme concentration and reaction conditions.

Another technique describes reversible solid-phase attachment of polymerase HSA fusion protein to achieve hot start. Nilsson et al., *BioTechniques* 22 (4), p. 744 (1997).

Accordingly, there remains a need for a simplified method and reagents for inhibiting or preventing non-specific nucleic acid extension and/or amplification in a PCR reaction.

SUMMARY OF THE INVENTION

The present invention provides a nucleic acid based polymerase inhibitor and methods of using the same in nucleic acid amplification reactions. One embodiment provides a polymerase inhibitor that includes a nucleic acid sequence, at least a portion of which is double-stranded at or below the melting temperature of the nucleic acid sequence. In some embodiments, the double-stranded portion of the nucleic acid sequence is of sufficient length to be recognized by a polymerase as a template for extension, except that the nucleic acid sequence is substantially incapable of being extended by the polymerase. Additionally, in some embodiments, at least one 3' terminal nucleic acid of the nucleic acid does not need to pair with at least one terminal 5' nucleic acid of the nucleic acid when the nucleic acid is double-stranded.

In exemplary embodiments, the polymerase inhibitor is not specific for a nucleic acid polymerase or family of polymerases related to the nucleic acid polymerase. Similarly, in some embodiments, the inhibitory activity of the polymerase inhibitor is not sequence specific. In some of the described embodiments, the nucleic acid sequence of the polymerase inhibitor does not act as a primer for an intended target nucleic acid. In still other embodiments, the nucleic acid sequence of the polymerase inhibitor does not form part of the nucleic acid that includes an intended target nucleic acid sequence. In further embodiments, the polymerase inhibitor consists essentially of a nucleic acid sequence. In yet more embodiments, at least the 5' terminal nucleic acid of the nucleic acid sequence is single stranded when the nucleic acid is at or below the melting temperature of the nucleic acid sequence. In additional embodiments, the 3' terminal nucleic acid of the nucleic acid sequence comprises a blocking moiety that prevents extension of the 3' terminal nucleic acid by the polymerase. In yet other embodiments, the portion of the nucleic acid that is double-stranded at or below the melting temperature of the nucleic acid is formed by a single nucleic acid sequence that is capable of annealing to itself.

In some embodiments, the portion of the nucleic acid that is double-stranded at or below the melting temperature of the nucleic acid is formed by two separate nucleic acid sequences that at least partially anneal to one another. As used herein separate nucleic acid sequences means that the nucleic acid sequences are not part of an unbroken, continuous sequence of nucleic acids. For example separate nucleic acids can include distinct nucleic acids that are not physically joined together or two nucleic acid sequences that are part of the same physical entity as long as the nucleic acid sequences are separated by a non-nucleic acid spacer or linking group. In additional embodiments, at least the 3' terminal nucleic acid of the nucleic acid sequence is single stranded when the nucleic acid is at or below the melting temperature of the nucleic acid sequence. In still more embodiments, the nucleic acid portion of the polymerase inhibitor includes DNA or a DNA mimetic or an RNA or an RNA mimetic. In some embodiments, the nucleic acid portion of the polymerase inhibitor is resistant to exonuclease degradation. In still further embodiments, the melting temperature of the double stranded portion of the nucleic acid portion of the polymerase inhibitor is in the range of about 25° C. to 80° C. In certain embodiments, the double stranded portion of the nucleic acid portion of the polymerase inhibitor is at least 10 bases in length.

Also provided is a method for inhibiting a nucleic acid polymerase, that includes adding any of the polymerase inhibitors to a nucleic acid to a reaction mixture that is to undergo a nucleic acid amplification reaction or performing a nucleic acid amplification reaction in the presence of a described polymerase inhibitor. Certain methods further include using one or more additional polymerase inhibitors whose nucleic acid portions have different melting temperatures. Still further methods include performing the nucleic acid amplification reaction on the reaction mixture, wherein the reaction mixture is capable of undergoing nucleic acid amplification when one or more target nucleic acids are present. In some of the methods the polymerase inhibitor is present at a ratio of 1×10E-12 mol decoy per unit of polymerase to 1×10E-10 mol decoy per unit of polymerase persists at a low concentration throughout the nucleic acid amplification reaction. In additional methods, the polymerase inhibitor is present in an amount that inhibits substantially all of the polymerase. Still further methods include detecting the presence or absence of any nucleic acid produced by the nucleic acid amplification reaction and/or quantifying the amount of any nucleic acid produce in the nucleic acid amplification reaction. In certain methods the polymerase inhibitor is not displaced from the polymerase enzyme by a primed target nucleic acid.

The present invention also provides kits for performing the present methods.

BRIEF DESCRIPTION OF THE DRAWINGS

FIGS. 1A and 1B are hairpin decoys. Hairpin decoys are single oligonucleotides containing self-complementary sequences that self-hybridize to form a partial duplex with a 5' extension or tail and a 3' end that cannot be extended by polymerase. The left column of FIG. 1A discloses SEQ ID NOS 11, 11, 12, 12, 13, 13, 14, 14, 10 and 10, respectively, in order of appearance. The right column of FIG. 1A discloses SEQ ID NOS 15, 15, 16, 16, 17, 17, 18 and 18, respectively, in order of appearance. The left column of FIG. 1B discloses SEQ ID NOS 19-25, 19, 19, 20, 20, 21, 21, 22, 22, 23, 23, 24, 24, 25 and 25, respectively, in order of appearance. The right column of FIG. 1B discloses SEQ ID NOS 12 and 12.

FIG. 2 illustrates duplex decoys. Duplex decoys are formed by hybridizing two oligonucleotides containing complementary sequences to form a partial duplex with a 5' extension or tail and a 3' end that cannot be extended by polymerase. FIG. 2 discloses SEQ ID NOS 26, 4, 27-28, 7, 6, 5 and 29-37, respectively, in order of appearance.

FIGS. 3 and 4 are examples of a technique to prevent further extension of the 3' ends of the extended primers oligonucleotides by placing a non-standard base (X) at the 5' end of each oligonucleotide primer and providing a triphosphate form of the orthogonal non-standard base (Z) to the amplification reaction.

Figure 5B:
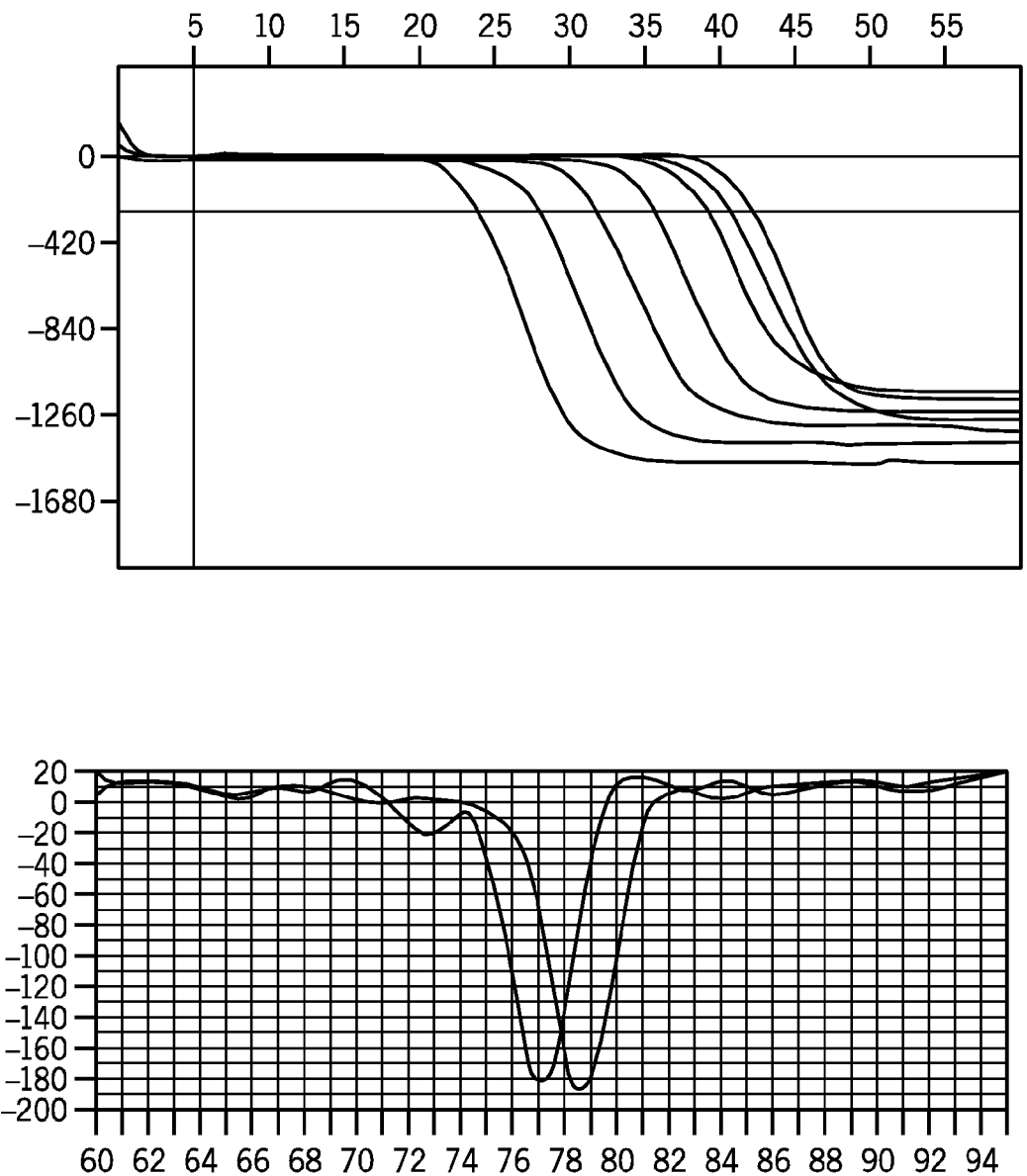
FIG. 5 shows a dilution series consisting of concentrations ranging from 100,000 to 0.1 molecules, plus a no target control was amplified in the presence of no decoy (FIG. 5A), 5
Figure 5D:
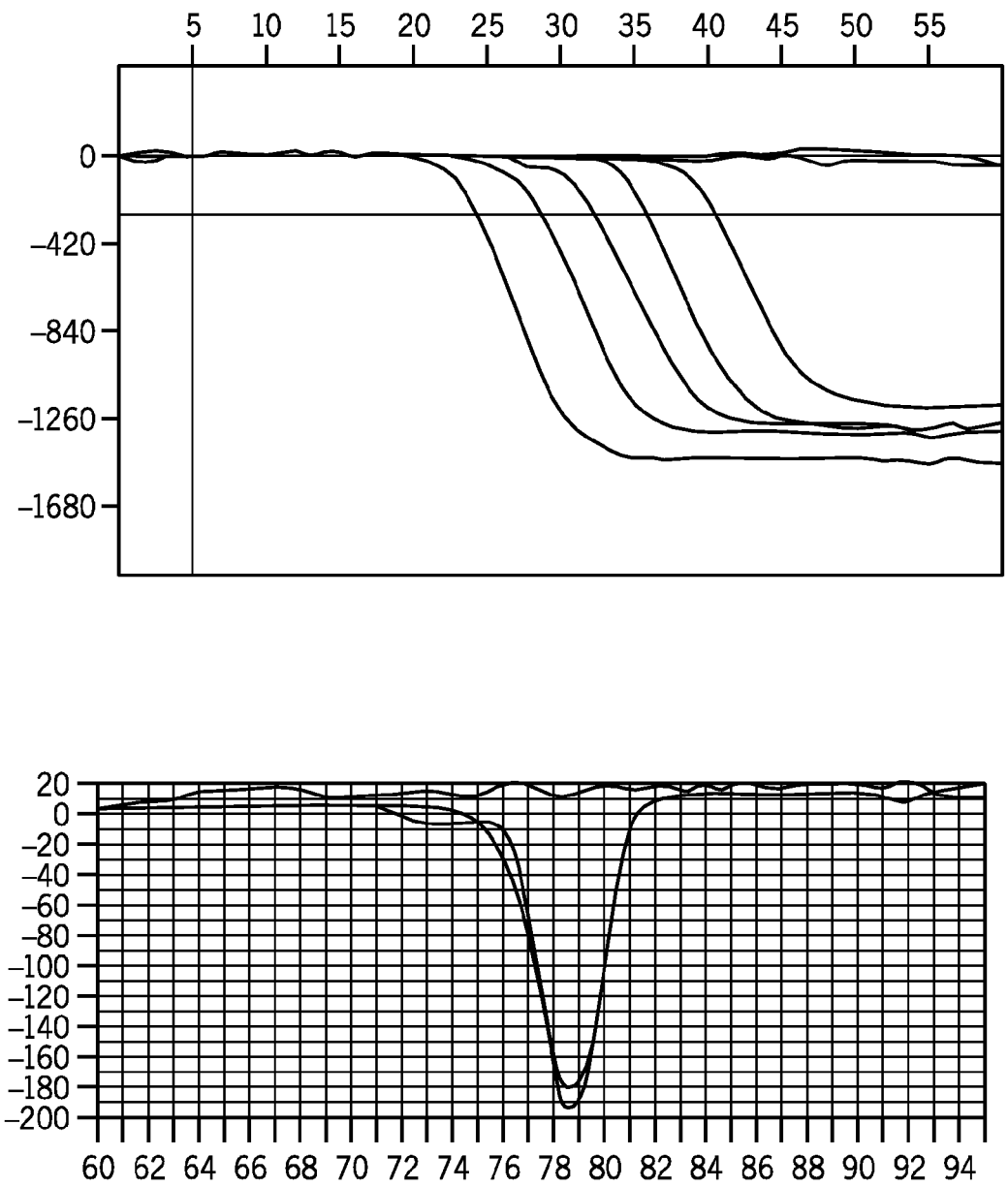

µM MM309/310 (FIG. 5B), 5 µM MM309/311 (FIG. 5C), and 5 µM MM309/312 (FIG. 5D).

Figure 6:
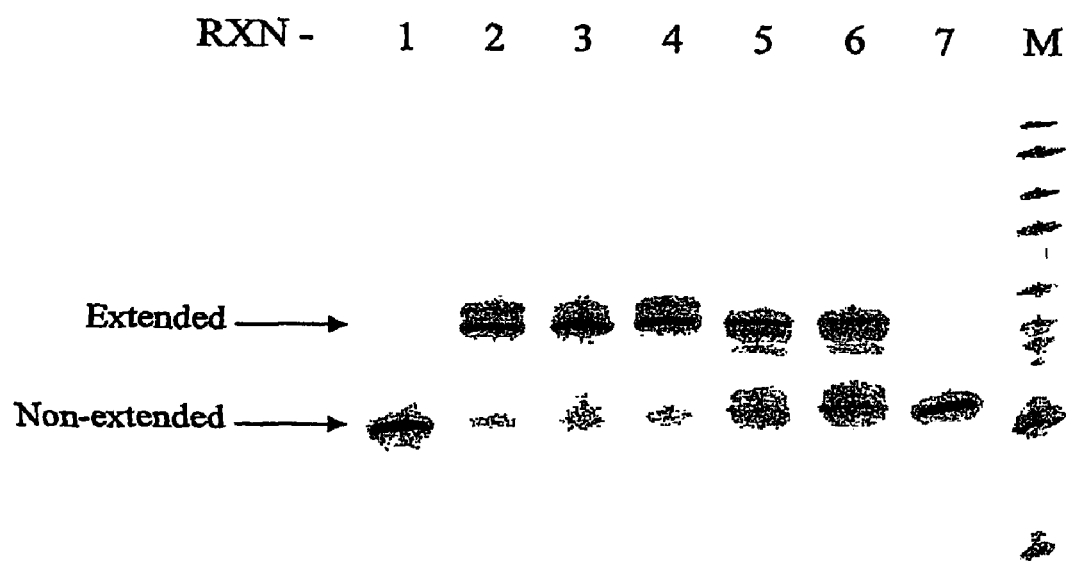

FIG. 6 illustrates selective inhibition of MMLV reverse transcriptase via a fluorescent image of the gel was obtained by scanning for 6FAM.

DETAILED DESCRIPTION

The present invention provides a nucleic acid based polymerase inhibitor that inhibits the activity of a polymerase below a given temperature, generally the temperature at which non-specific priming and extension occurs, but allows for polymerase activity above the given temperature, which is generally the temperature at which a primer anneals specifically to a target nucleic acid. As used herein a "nucleic acid based polymerase inhibitor" or in some instances simply "polymerase inhibitor" describes a polymerase inhibitor at least partially composed of a nucleic acid. In some embodiments, particularly when the temperature of the reaction mixture is below the given temperature, the nucleic acid portion of the polymerase inhibitor is at least partially double stranded and the partially double stranded portion of the nucleic acid is of sufficient length to be recognized by a polymerase, at least potentially as a substrate for extension. The nucleic-acid based polymerase inhibitor can be composed entirely of, or almost entirely of nucleic acids, whereas in other embodiments the nucleic acid can be joined to a non-nucleic acid moiety, such as a protein, blocking group, label or the like. When present, the double stranded portion of the nucleic acid can result from a single oligonucleotide annealed with itself, such as by forming a hairpin-like or stem-loop structure, or two or more separate oligonucleotides annealed together. Generally, the polymerase inhibitor comprises two oligonucleotides because the melting behavior are more favorable and allow more rapid denaturation kinetics with a narrower range than a single oligonucleotide that self-anneals. Thus, the nucleic acid based polymerase inhibitor can be composed of two or more individual entities, which can both be nucleic acids or one of which can be a ligand, such as a protein or nucleic acid mimic, that binds the other portion of the nucleic acid based polymerase inhibitor. Two separate oligonucleotides that form the double stranded portion of the nucleic acid can have the same or different sequence. Providing oligonucleotides that anneal to themselves or other oligonucleotides can be achieved through various means known in the art, including providing portions of the nucleic acid that are complementary to each other or providing a palindromic sequence within the nucleic acid. In some of these embodiments, the nucleic acid base polymerase inhibitor can have an extended 5' tail and a free 3' end. The preferred range of length is 7-16 bp 5' tail and duplex regions from 5 to 16 bp were tested with 10 or greater seeming to work the best.

In some embodiments, the nucleic acid based polymerase inhibitor or a portion thereof can double as the primer for the target nucleic acid in the PCR reaction, provided that the double stranded portion of the nucleic acid based inhibitor is sufficiently long to be recognized by the polymerase enzyme as a substrate for extension. Without limiting the scope of the invention, generally the double stranded portion of the nucleic acid based polymerase inhibitor will be at least 10 base pairs long, although shorter double stranded segments are permissible as long as they are recognized by the polymerase as substrates for extension. In other embodiments, the nucleic acid portion of the polymerase inhibitor does not act as a primer for the target nucleic acid in the PCR reaction. Similarly, the nucleic acid based polymerase inhibitor does not generally form part of the target nucleic acid. In the case where a portion of the nucleic acid based polymerase inhibitor also acts as primer for the target nucleic acid, the polymerase inhibitor should not be a single oligonucleotide that anneals to itself forming only a short double-stranded portion that is not recognized as a substrate for extension and only serves to fold the primer into a conformation that will not anneal to the target nucleic acid until the double-stranded portion of the nucleic acid is melted, such as a double-stranded portion only 5 or 6 base pairs in length.

Generally, the present polymerase inhibitors, and in particular those formed by self-annealing of a single stranded nucleic acid, are also not specific for a particular polymerase, a family of related polymerases, or polymerases that share a high degree of similarity or sequence homology. One skilled in the art will be available to identify polymerase enzymes that fall within a family of related polymerases using known guidelines, such as the organism from which the polymerase is obtained and its phylogenetic classification, sequence similarity and identity, etc. As a non-limiting example, polymerase enzymes obtained from the *Thermus* family (such as Tbr polymerase from *Thermus brockianus*, Tfl polymerase from *Thermus flavus*, Tma polymerase from *Thermotoga maritima* and Tth polymerase from *Thermococcus thermophilus*) are generally considered to be related due to their sequence homology. The Tth polymerase and Taq polymerase are reported to be 93% similar and 88% identical at the amino acid sequence level (Abramson (1995) in *PCR Strategies* (Academic Press, New York). Tfl polymerase is reported to be 93% similar and 86% identical to Taq polymerase at the amino acid level (U.S. Pat. No. 6,183,967). In contrast Tma polymerase from *Thermotoga maritima* and Tli polymerase from *Thermococcus litoralis* are usually not considered to be closely related to polymerase from the *Thermus* family. Tli polymerase shares little sequence homology with eubacterial enzymes (Ito and Braithwaite (1991) *Nucleic Acids Res.* 19:4045). Tma polmerase is reported to be 61% similar and 44% identical to Taq polymerase at the amino acid level (Abramson (1995) in *PCR Strategies* (Academic Press, New York). Another measure of relatedness between polymerase enzymes can be found in U.S. Pat. Nos. 5,693,502, 5,763,173, 5,874,557, 6,020,130, and 6,183,967 which measures relatedness of polymerase enzymes by their inhibition resulting from families of specific aptamers.

In further embodiments, the present polymerase inhibitors and methods may be designed to persist at low concentrations even during the higher, more target nucleic acid specific temperatures achieved during the reaction, thus continuing to compete with non-specific interactions and extension throughout the amplification without blocking PCR. In this embodiment, as well as others, the methods described herein can use one or more polymerase inhibitors, such as 2, 3, 4, 5, 6, 7, 8, 9 or 10, that have different Tm characteristics, providing for precise control and inhibition of non-specific interactions at multiple temperatures. The concentrations of the different polymerase inhibitors can be varied as desired and generally at lower temperatures more polymerase inhibitors will be present in the reaction mixture whereas at higher temperatures fewer polymerase inhibitors will be present to compete with target nucleic acid extension.

The present invention also provides methods of performing nucleic acid amplification reaction that involve adding the nucleic acid based polymerase inhibitor to a reaction mixture that is to undergo a nucleic acid amplification reaction. The reaction mixture can contain all, or only some, of the components necessary to perform the nucleic acid amplification. Generally, the components required for the nucleic acid amplification include buffer, magnesium ion, nucleotides that can be incorporated onto a nucleic acid, such as deoxynucleotides, polymerase enzyme and one or more primers. One skilled in the art will recognize that a successful PCR reaction will not occur in the absence of a target nucleic acid although the presence of a target nucleic acid is not required to perform the present methods. Any components required for the amplification reaction that are not present when the polymerase inhibitor is present can be subsequently added to the reaction mixture. In some embodiments, the nucleic acid based polymerase inhibitor is present in an amount sufficient to inhibit substantially all of the polymerase to be used in the reaction mixture. The optimal concentration of nucleic acid based polymerase inhibitor can be easily determined by one skilled in the art. In some embodiments, the polymerase inhibitor is present at a ratio of 1×10E-12 mol decoy per unit of polymerase to 1×10E-10 mol decoy per unit of polymerase where a unit is defined to be the amount of enzyme that will incorporate 10E-8 mol of dNTPs into acid insoluble material per 30 minutes at reaction temperature.

The methods described herein can further involve performing the nucleic acid amplification reaction on the reaction mixture that is capable of undergoing nucleic acid amplification when one or more target nucleic acids are present and that contains the nucleic acid based polymerase inhibitor. In some of the present methods, the nucleic acid amplification can be set up to achieve linear amounts of amplification, as discussed in Stump et al., *Nucleic Acids Res* 27 (23), p. 4642 (1999), or exponential growth of amplification. Additionally, in other methods, the nucleic acid amplification is not a hairpin extension assay as disclosed in Kainz et al., *BioTechniques* 28, p. 278 (2000). In some embodiments, the methods described herein are carried out under thermal cycling conditions, and not isothermal conditions. The target nucleic acid can be provided or isolated from a sample having or suspected of having a specific nucleic acid sequence. After the nucleic acid amplification is performed, the presence or absence of the target nucleic acid can be determined or its amount measured. In order to facilitate detection or quantitation of the nucleic acid products, one or more of the primers used in the amplification reaction can be labeled. Similarly, the efficiency of any nucleic acid amplification can also be measured an/or compared against a control reaction that has the same component as the nucleic acid amplification reaction except for the polymerase inhibitor. In this manner, the effectiveness of the different nucleic acid based polymerase inhibitors can be measured.

In performing the amplification reaction, it is believed that the double stranded portion of the nucleic acid based inhibitor is recognized by the polymerase as a suitable substrate or template for nucleic acid extension, and thus the polymerase will bind to the double-stranded portion of the nucleic acid based polymerase inhibitor. As the polymerase binds to the double stranded portion of the polymerase inhibitor, the polymerase inhibitor should generally be incapable of being extended by the polymerase so as to prevent non-specific extension. The manner of preventing the polymerase from extending the polymerase inhibitor is not particularly limited and can be achieved by several techniques, which include having isobases in a 5' extension of the nucleic acid, or chemically modifying or capping the 3' end of the nucleic acid, such as by using a non-extendable nucleotide or blocking moiety. Exemplary blocking groups are biotin, di-deoxynucleotide triphosphates ("ddNTPs"), also referred to as chain terminating ddNTPs, and ethylene glycol linkers on the 3' OH. In other methods, the oligonucleotide that is made non-extendable by adding bases to the 3' end that are not complementary to the target sequence and therefore do not base-pair and cannot be enzymatically extended.

Generally, the present polymerase inhibitors will not be a nucleic acid where the 5'-terminal base of the nucleic acid pairs with the 3'-terminal base of a complementary nucleic acid, such as where two nucleic acids are complementary to one another or a single nucleic acid has self-complementary sequences at the 3' and 5' ends. Examples of such nucleic acids are found in Kainz et al., *BioTechniques* 28, p. 278 (2000) and U.S. Pat. No. 5,565,340, respectively.

Alternatively, the 3' end of the nucleic acid may be capped using non-standard bases such as, but not limited to, AEGIS™ bases. Various amplification systems, for example but not limited to PCR, TMA, SDA, NASBA, depend in part upon the ability of a nucleic acid polymerase to extend off the 3' hydroxyl of an oligonucleotide primer. Specificity of these reactions depends in part on the careful design of these oligonucleotide primers. One important factor in the design of these amplification systems is the extension of 3' hydroxyl of the oligonucleotides to create new 3' sequences. These sequences may be predicted as is the case in an intended amplification product (FIG. 3) or unintended (FIG. 4). FIGS. 3 and 4 are examples of a technique to prevent further extension of the 3' ends of the extended primers oligonucleotides by placing a non-standard base (X) at the 5' end of each oligonucleotide primer and providing a triphosphate form of the orthogonal non-standard base (Z) to the amplification reaction. The installation of the Z nucleoside at the 3' position of the oligonucleotide extension product is intended to render that nucleotide sequence resistant to further extension under the conditions of the amplification reaction. The Z nucleoside may be selected from, but not limited to K, X, isoG, or isoC. The Z nucleoside may be, but not limited to, the ribo, deoxy, dideoxy, or acyclo form of the nucleoside.

Because the polymerase does not extend the polymerase inhibitor, the polymerase becomes bound to, and sequestered or trapped by, the polymerase inhibitor. Upon the heating that occurs in the normal PCR reaction, the temperature of the reaction mixture will rise above the melting temperature (Tm) of the double stranded portion of the nucleic acid based polymerase inhibitor. This temperature rise results in denaturation of the double stranded portion of the polymerase inhibitor and release of the polymerase enzyme. After the polymerase enzyme is released, it can then perform its normal function in the polymerase reaction of extending any primed target nucleic acid sequences present. Preventing or inhibiting non-specific nucleic acid extension and mis-priming via the present methods allows more efficient amplification of any target nucleic acid present resulting in a higher fidelity reaction. Thus, the present methods provide higher sensitivity and consistently higher results than regular PCR techniques.

When the temperature of the PCR mixture returns to at or below the Tm of the nucleic acid based polymerase inhibitor, the nucleic acid portion at least partially reanneals forming the double stranded structure that sequesters the polymerase enzyme. Thus, the nucleic acid based polymerase inhibitor can be reversible depending upon the temperature of the reaction mixture. This is advantageous because non-specific priming and extension is prevented not only prior to the first nucleic acid extension or amplification, as is the case with many hot-start PCR techniques, but also during the period between the cycles of specific target dependent extension. In this manner, the nucleic acid based polymerase inhibitor acts as a decoy or reversible sink for the polymerase enzyme. As such, the sequence of the nucleic acid portion of the polymerase inhibitor is not particularly limited, i.e. inhibition is not sequence specific, as long as it has the desired Tm characteristics.

The Tm of the double stranded portion of the nucleic acid based polymerase inhibitor can be designed, modified or calculated by one skilled in the art using known techniques. Preferably, the Tm of the double stranded portion of the polymerase inhibitor will be about the temperature at which specific priming of the target nucleic acid and extension thereof by the polymerase predominates over non-specific priming and extension. Generally, this temperature will be in the range from about 25° C. to 80° C. depending on the desired decoy characteristics. Parameters affecting Tm include primer length, concentration of primers in the reaction, relative G/C content, uniqueness, self-complementarity, complementarity with other primers, sequence composition, and 3' end sequence of the primer. The longer the primer and higher G/C percentage, the higher the denaturation and annealing temperature. The temperature at which the primers and template nucleic acid denature and anneal can also be affected by stringency of the reaction mixture which includes pH, concentration of monovalent cations, divalent cations and presence of organic solvents.

Variables affecting stringency include, for example, temperature, salt concentration, probe/sample homology, nucleic acid length and wash conditions. Stringency is increased with a rise in hybridization temperature, all else being equal. Increased stringency provides reduced non-specific hybridization. i.e., less background noise. "High stringency conditions" and "moderate stringency conditions" for nucleic acid hybridizations are explained in Ausubel et al., *Cur Prot Mol Biol,* 1998, Green Publishing Associates and Wiley Interscience, N.Y. Of course, the artisan will appreciate that the stringency of the hybridization conditions can be varied as desired, in order to include or exclude varying degrees of complementation between nucleic acid strands, in order to achieve the required scope of detection. Likewise the protein and nucleic acid can be interacted under varying conditions which either enhance or interfere with protein-nucleic acid interactions.

Unlike other methods, the present polymerase inhibitors do not require or rely on degradation of the nucleic acid base polymerase inhibitor, for example at the 3' end, so that the polymerase inhibitor can then act as a primer. Examples of such methods are disclosed in U.S. Pat. Nos. 6,482,590 and 6,274,353. In some embodiments, the polymerase has higher affinity for the nucleic acid based polymerase inhibitor than other non-specific substrates, such as primer-dimers. Additionally, in some embodiments, the present polymerase inhibitors are not specific for a single polymerase and can be used to inhibit two or more different, unrelated, polymerases. As such the present invention does not utilize inhibitors found using the SELEX method, such as disclosed in U.S. Pat. Nos. 5,693,502, 5,763,173, 5,874,557, 6,020,130, and 6,183,967 and Dang et al. *J Mol Biol* 264 (2), p. 268 (1996). The present polymerase inhibitors can also be used in conjunction with the methods described in these patents.

The polymerase used in the present methods and kits is not particularly limited, and any suitable polymerase can be used. For example, the polymerases are thermally stable DNA polymerases. Some examples of thermally stable DNA polymerases include, but are not limited to, *Thermus aquaticus* DNA polymerase, N-terminal deletions of Taq DNA polymerase such as Stoffel fragment DNA polymerase, Klentaq235, and Klentaq-278; *Thermus thermophilus* DNA polymerase; *Bacillus caldotenax* DNA polymerase; *Thermus flavus* DNA polymerase; *Bacillus stearothermophilus* DNA polymerase; and archaebacterial DNA polymerases such as *Thermococcus litoralis* DNA polymerase (also referred to as Vent), Pfu, Pfx, Pwo, and Deep Vent or a mixture of DNA polymerases. The present invention can also utilize various reverse transcriptases when the nucleic acid based polymerase inhibitor is recognized by the reverse transcriptase. Some examples of reverse transcriptases include but are not limited to those from avian myeloblastosis virus (AMV), moloney murine lukemia virus (M-MLV), modified M-MLV reverse transcriptase, and human immunodeficiency virus (HIV). Polymerase inhibitors recognizable by reverse transcriptases can include either deoxy-ribonucleic acids, ribonucleic acids or more stable mimics of ribonucleic acids such as 2'-O-methyl nucleotides or mixtures thereof. Those inhibitors derived from ribonucleotides, ribonucleotide derivatives or mixtures of ribonucleotides and deoxynucleotides are expected to be reverse transcriptase or RNA-dependent DNA polymerase specific. Inhibitors comprised entirely of deoxynucleotides will inhibit both DNA polymerases and reverse transcriptases. Inhibitors derived solely from ribonucleotides and ribonucleotide derivatives should inhibit RNA-dependent RNA polymerase as well as reverse transcriptases. Preferred polymerases have low error rates. As polymerases are known to have different enzymatic activities other than catalyzing nucleic acid synthesis, such as exonuclease activity, the present polymerase inhibitors are directed to the polymerase activity of the polymerase. Additionally, the nucleic acid portions of the polymerase inhibitor are resistant to degradation, such as through exonuclease activity.

As used herein "nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases. Accordingly, the nucleic acids described herein include not only the standard bases adenine (A), cytosine (C), guanine (G), thymine (T) and uracil (U) but also non-standard (AEGIS™) bases. Non-standard bases, which form hydrogen-bonding base pairs, are described, for example, in U.S. Pat. Nos. 5,432,272, 5,965,364, 6,001,983, 6,037,120, and 6,140,496, all of which are incorporated herein by reference. By "non-standard base" it is meant a base other than A, G, C, T, or U that is susceptible of incorporation into an oligonucleotide and which is capable of base-pairing by hydrogen bonding, or by hydrophobic, entropic, or van der Waals interactions to form base pairs with a complementary base. Specific examples of these bases include the following bases in base pair combinations (iso-C/iso-G, K/X, H/J, and M/N):

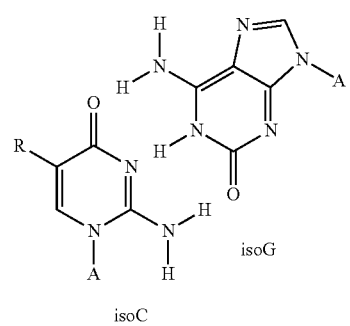

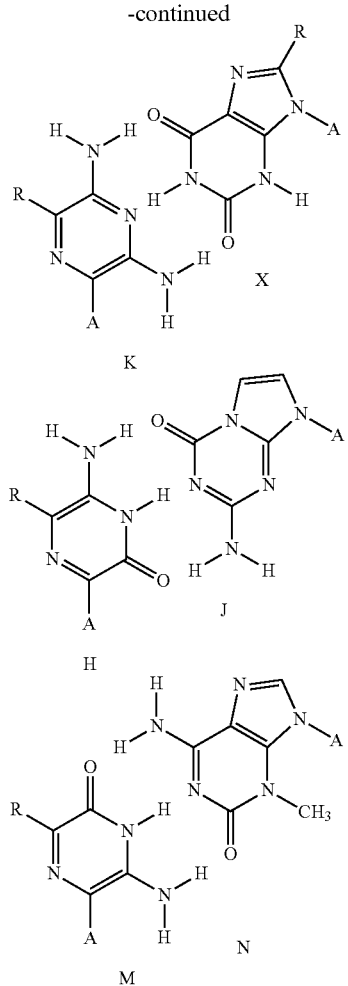

where A is the point of attachment to the sugar or other portion of the polymeric backbone and R is H or a substituted or unsubstituted alkyl group. It will be recognized that other non-standard bases utilizing hydrogen bonding can be prepared, as well as modifications of the above-identified non-standard bases by incorporation of functional groups at the non-hydrogen bonding atoms of the bases. To designate these non-standard bases in FIGS. 3 to 9, the following symbols will be used: X indicates iso-C and Y indicates iso-G.

The hydrogen bonding of these non-standard base pairs is similar to those of the natural bases where two or three hydrogen bonds are formed between hydrogen bond acceptors and hydrogen bond donors of the pairing non-standard bases. One of the differences between the natural bases and these non-standard bases is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-standard bases for use in oligonucleotides include, for example, naphthalene, phenanthrene, and pyrene derivatives as discussed, for example, in Ren et al., *J. Am. Chem. Soc.* 118, 1671 (1996) and McMinn et al., *J. Am. Chem. Soc.* 121, 11585 (1999), both of which are incorporated herein by reference. These bases do not utilize hydrogen bonding for stabilization, but instead rely on hydrophobic, entropic, or van der Waals interactions to form base pairs.

The present nucleic acids can also utilize 2' O-methyl nucleotides which mimic RNA providing polymerase inhibitors specific for reverse transcriptase enzymes.

As used herein, the term "target" DNA or nucleic acid refers to that polynucleotide material to be amplified in the DNA or nucleic acid sample. The term "non-target" refers to that polynucleotide material for which amplification is not desired. A DNA fragment in a sample is either a "target" or a "non-target" DNA. As used herein, the term "primer" has the conventional meaning associated with it in standard PCR procedures, i.e., an oligonucleotide that can hybridize to a polynucleotide template and act as a point of initiation for the synthesis of a primer extension product that is complementary to the template strand.

Any or all of the oligonucleotides described herein can be labeled, and for many purposes, it is desirable that at least one of the oligonucleotides be labeled. Additionally, the dNTPs can be labeled. Beneficially, when an oligonucleotide is labeled, the label can be conjugated to the 3' thereof such that elongation from the 3' end thereof is not possible. Exemplary labeling protocols are well known; see, e.g., European Patent Appln. 292128.

The labels can facilitate either the direct, proximal or indirect detection and/or capture of the amplified product. Additionally, two of the moieties can be part of a unitary structure such that only two oligonucleotide moieties are utilized in the amplification reaction. As used herein, a label that is directly detectable produces a signal which is capable of detection either directly or through its interaction with a substance such as a substrate (in the case of an enzyme), a light source (in the case of a fluorescent compound) or a photomultiplier tube (in the case of a radioactive or chemiluminescent compound).

Examples of preferred direct labels include radioisotopic labels, e.g., the use of oligonucleotides which have incorporated $^{32}P$, $^{35}S$, $^{125}I$, $^{3}H$, $^{14}C$. One approach for direct labeling of oligonucleotides is the end-labeling approach whereby T4 polynucleotide kinase is used to introduce a label into the 5' terminus of the oligonucleotide (See, e.g., Richardson, C. C., *The Enzymes*. Vol. XIV, *Nucleic Acids* Part A, Ed. Boyer, P. D., Acad. Press, p. 299 (1981)). Alternatively, terminal deoxynucleotidyl transferase can be utilized to add a series of supplied deoxynucleotides onto the 3' terminus of the oligonucleotide; single nucleotide labeling methods can also be used (See, e.g. Bollum, F. J. *The Enzymes*, Vol. X, Ed. Boyer, P. D. Acad. Press, (1974); Yousaf, S. I. et al., *Gene* 27, p. 309 (1984); and Wahl, G. M. et al. *Proc Natl Acad Sci* (U.S.A.) 76, pp. 3683-3687 (1979). Labeled ddNTPs, e.g., $^{32}P$ ddATP, can also be utilized.

A label that is indirectly detectable does not in and of itself provide a detectable signal; it can, however, be used to identify an oligonucleotide to which the indirectly detectable label is attached. For example, an indirect label can be used in conjunction with another label to produce or quench a detectable signal (i.e., an indirect label can be a quencher of a quencher-dye pair). Preferably, the quencher-dye pair is comprised of a fluorophore and a quencher. Suitable fluorophores include, for example, fluorescein, cascade blue, hexachloro-fluorescein, tetrachloro-fluorescein, TAMRA, ROX, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaza-S-indacene-propionic acid, 6-carboxy-X-rhodamine, N,N,N',N'-tetramethyl-6-carboxyrhodamine, Texas Red, Eosin, fluorescein, 4,4-difluoro-5,7-diphenyl-4-bora-3a,4a-diaza-s-indacene-3- propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-5-indacene-propionic acid. Suitable quenchers include, for example, Dabcyl, QSY7™ (Molecular Probes, Eugene, Oreg.) and the like. In addition, dyes can also be used as a quencher if they absorb the emitted light of another dye.

Biotin, antibodies, enzymes, ferritin, antigens, haptens, etc. when conjugated to a dNTP or ddNTP comprise further examples of indirectly detectable labels. Preferred non-radioactive direct labels include fluorescein-11-dUTP (see Simmonds, A. C. et al Clin Chem 37, pp. 1527-1528 (1991), incorporated herein by reference) and digoxigenin-11 dUTP (see Muhlegger, K. et al. Nucleosides & Nucleotides 8, pp. 1161-1163 (1989), incorporated herein by reference) can be utilized as labels. Additionally, non-radioactively labeled oligonucleotides, such as hapten labeled oligonucleotides may be used (See, e.g., Adams, C. W., PCT Patent Appln. WO 91/19729). A detection scheme involving such hapten-labels includes utilization of antibodies to the hapten, the antibodies being labeled. Biotin is an especially preferred indirect label, whereby the detection of biotinylated nucleic acid molecules is accomplished using labeled or insolubilized avidin, streptavidin, anti-biotin antibodies, etc. Biotinylated molecules can also be readily separated from non-biotinylated molecules by contacting the molecules with insoluble or immobilized avidin.

In this regard, for example, biotin-11-dUTP can be utilized in lieu of dTTP, or biotin-14-dATP in lieu of DATP (See generally, Langer, P. R. et al., *Proc Natl Acad Sci* (U.S.A.) 78, pp. 6633-6637 (1981), which is incorporated herein by reference). Biotinylated phosphoramidites can also be used (Misiura, K. et al. *Nucl Acids Res* 18, pp. 4345-4354 (1990), which is incorporated herein by reference). Such phosphoramidites allows for precise incorporation thereof at desired locations along the growing oligonucleotide moiety during the synthesis thereof.

Chemiluminescent substrates can also be used as the indirect label. Enzymes, such as horseradish peroxidase ("HRP"), alkaline phosphatase ("AP"), etc. which can be directly cross-linked to nucleic acids may be employed (see, Renz, M. and Kurz, C. *Nucl. Acids Res.* 12, pp. 3435-3444 (1964), incorporated herein by reference). Luminal, a substrate for HRP, and substituted dioxetanes, substrates for AP, can be utilized as chemiluminescent substrates. xemplary of the HRP labeling protocol is the ECL system available from Amersham (Arlington Heights, Ill., USA).

In lieu of direct or indirect labels, a proximity label may be employed. Such a label is a chemical moiety which produces a signal only in the presence of a second label which interacts with it. Typically, a first proximity label is used in combination with a corresponding second proximity label.

It will be understood to those skilled in the art that the present methods readily lends themselves to automation.

The present oligonucleotides and methods can be carried out by made or performing any of the characteristics described herein, either alone or in various combination.

Additionally, one skilled in the art will realize that the present invention also encompasses variations of the present oligonucleotides and methods that specifically exclude one or more of the characteristics described above.

The present invention also provides kits for carrying out the methods described herein. In one embodiment, the kit is made up of instructions for carrying out any of the methods described herein. The instructions can be provided in any intelligible form through a tangible medium, such as printed on paper, computer readable media, or the like. The present kits can also include one or more reagents, buffers, hybridization media, nucleic acids based polymerase inhibitors, nucleic acids, primers, nucleotides, molecular weight markers, enzymes, solid supports, databases, computer programs and/or disposable lab equipment, such as multi-well plates, in order to readily facilitate implementation of the present methods. Enzymes that can be included in the present kits include DNA polymerases, and the like. Solid supports can include beads and the like whereas molecular weight markers can include conjugatable markers, for example biotin and streptavidin or the like. The kit components can be packaged in the same or separate containers as desired. Examples of preferred kit components can be found in the description above and in the following examples.

EXAMPLES

Example 1

Demonstration of decoy effects on primer dimer formation in real time PCR. Reactions were set-up as follows: 1 µl 10×PCR buffer (100 mM BTP pH 9.1, 400 mM KAc, 20 mM $MgCl^2$, 1 mg/ml BSA), 100 µM each dATP, dTTP, dCTP, dGTP (Promega), 3 µM dabcyl iGTP (EraGen Biosciences), 200 nM forward PCR primer CL025 (5' FAM-TXGATAG-CAACAATTCATCTACAGA), (SEQ ID NO:1), 200 nM reverse PCR primer CL026 (5' ATGGGTAGTGAATGATC-TITGTTTC) (SEQ ID NO:2), 1 U KlenTaq (Ab peptides) and 5 µl synthetic DNA target CL021 (5' TCAGATAGCAA-CAATTCATCTACAGACCCAATTAGCAGT GGAGAAA-CAAGATCATTCACTACCCATTTCT-TAACTTATCCCAAGATAGGACT TCTGTACA) (SEQ ID NO:3). A dilution series consisting of concentrations ranging from 100,000 to 0.1 molecules, plus a no target control was amplified in the presence of no decoy (FIG. 5A), 5 µM MM309/310 (FIG. 5B), 5 µM MM309/311 (FIG. 5C), and 5 µM MM309/312 (FIG. 5D). The PCR thermocycling was performed in an iCycler (Bio-Rad) with the following cycling conditions: 2 minute 94° denature, PCR 60 rounds: 1 sec 94°, 1 sec 58°; 20 sec 72° with optical reading. After PCR cycling a melt analysis was performed. The samples were heated from 60° to 95° with optical reads at every 0.5° increment.

| | |
|---|---|
| 5' GCTGTCTGGTCCGTTATTATAC-PO4<br>MM309 | (SEQ ID NO: 4) |
| 3' ddC AATAATATG<br>MM310 Tm = 24.3° | (SEQ ID NO: 5) |
| 3' ddCAGGCAATAATATG<br>MM311 Tm = 40.5° | (SEQ ID NO: 6) |
| 3' ddCCAGGCAATAATATG<br>MM312 Tm = 45° | (SEQ ID NO: 7) |

Example 2

Selective inhibition of MMLV reverse transcriptase.

CL001
(SEQ ID NO: 8)
GCTGTCTGGTCCGAAACGATCGGGATTTTTTTTAAAATCCCGATCGTT

TCdd

CL002
(SEQ ID NO: 9)
<u>GCTGTCTGGTCCGAAACGATCGGGATTTTTTTT</u>AAAATCCCGATCGTT

TCdd (UNDERLINED BASES ARE 2' O-methyl)
(SEQ ID NO: 10)
DM436 FAM-TXAGAGTCTGGTGCCGACTCGACGTTTTCGTCGAGTCG Reactions 1-7 all contained the following: 10 mM Bis-Tris-Propane pH 9.1, 40 mM KCl, 2 mM $MgC^{12}$, 0.1 mg/ml BSA, 5 mM DTT, 100 µM dGTP, 100 µM DATP, 100 µM dTTP, 100 µM dCTP, 200 nM DM436. Individual component in reactions 1-7 were prepared as indicated in the table below.

| Reaction | KlenTaq | MMLV | Decoy (1 µM) |
| --- | --- | --- | --- |
| 1 | (—) | (—) | (—) |
| 2 | 1 unit | (—) | (—) |
| 3 | 1 unit | (—) | CL001 |
| 4 | 1 unit | (—) | CL002 |
| 5 | (—) | 5 units | (—) |
| 6 | (—) | 5 units | CL001 |
| 7 | (—) | 5 units | CL002 |

These reactions were incubated at 40° C. for 10 minutes, then stopped by the addition of 10 µl formamide to each tube. The resulting mixtures were incubated at 95° C. for 2 minutes prior to subjecting 5 µl of each of these samples to denaturing PAGE (8% polyacrylamide, 7M urea, 40% formamide, 0.5× TBE). FIG. 6 shows a fluorescent image of the gel was obtained by scanning for 6FAM using a Typhoon™ fluorescence scanner (Molecular Dynamics, Sunnyvale, Calif.).

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group or genus, but also the main group or genus absent one or more of the group members or species. The present invention also envisages the explicit exclusion of one or more of any of the group members or species from the main group or genus in the claimed invention.

All references disclosed herein are specifically incorporated by reference thereto.

While preferred embodiments have been illustrated and described, it should be understood that changes and modifications can be made therein in accordance with ordinary skill in the art without departing from the invention in its broader aspects as defined herein.

What is claimed is:

1. A method for inhibiting a nucleic acid polymerase, comprising performing a nucleic acid amplification reaction in the presence of a polymerase inhibitor, wherein the polymerase inhibitor comprises a nucleic acid sequence, a portion of which is double-stranded at or below the melting temperature of the nucleic acid sequence, wherein the double-stranded portion of the nucleic acid sequence is of sufficient length to be recognized by a polymerase as a template for extension, except that the nucleic acid sequence is substantially incapable of being extended by the polymerase, wherein at least a 5' nucleotide of the nucleic acid sequence is single stranded when the nucleic acid is at or below the melting temperature of the nucleic acid sequence.

2. The method of claim 1 further comprising one or more additional polymerase inhibitors whose nucleic acid portions have different melting temperatures.

3. The method of claim 1, wherein the polymerase inhibitor is present at a ratio of 1×10E-12 mol per unit of polymerase to 1×10E-10 mol per unit of polymerase.

4. The method of claim 1, wherein the polymerase inhibitor is present in an amount that inhibits substantially all of the polymerase.

5. The method of claim 1 further comprising detecting the presence or absence of any nucleic acid produced by the nucleic acid amplification reaction.

6. The method of claim 5 further comprising quantifying the amount of any nucleic acid produced in the nucleic acid amplification reaction.

7. The method of claim 1, wherein the polymerase inhibitor is not displaced from the polymerase enzyme by a primed target nucleic acid.

8. The polymerase inhibitor of claim 1, wherein the 3' terminal nucleic acid of the nucleic acid sequence comprises a blocking moiety that prevents extension of the 3'terminal nucleic acid by the polymerase.

9. The method of claim 1, wherein the portion of the nucleic acid that is double-stranded at or below the melting temperature of the nucleic acid is formed by a single nucleic acid sequence that is capable of annealing to itself.

10. The method of claim 1, wherein the portion of the nucleic acid that is double-stranded at or below the melting temperature of the nucleic acid is formed by two separate nucleic acid sequences that at least partially anneal to one another.

11. The method of claim 1, wherein at least the 3' terminal nucleic acid of the nucleic acid sequence is single stranded when the nucleic acid is at or below the melting temperature of the nucleic acid sequence.

12. The method of claim 1, wherein the nucleic acid portion of the polymerase inhibitor comprises DNA or a DNA mimetic.

13. The method of claim 1, wherein the nucleic acid comprises RNA or an RNA mimetic.

14. The method of claim 1, wherein the melting temperature of the double stranded portion of the nucleic acid portion of the polymerase inhibitor is in the range of about 25° C. to 80° C.

15. The method of claim 1, wherein the double stranded portion of the nucleic acid portion of the polymerase inhibitor is at least 10 bases in length.

* * * * *

SEQUENCE LISTING

```
<160> NUMBER OF SEQ ID NOS: 37

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: iso-c

<400> SEQUENCE: 1
tngatagcaa caattcatct acaga                                              25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```

```
atgggtagtg aatgatcttg tttc                                          24

<210> SEQ ID NO 3
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tcagatagca acaattcatc tacagaccca attagcagtg gagaaacaag atcattcact   60
acccatttct taacttatcc caagatagga cttctgtaca                        100

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctgtctggt ccgttattat ac                                            22

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: dideoxy-c

<400> SEQUENCE: 5
gtataataac                                                          10

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: dideoxy-c

<400> SEQUENCE: 6
gtataataac ggac                                                     14

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: dideoxy-c

<400> SEQUENCE: 7
```
gtataataac ggacc                                            15

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(51)
<223> OTHER INFORMATION: dideoxy-c

<400> SEQUENCE: 8
gctgtctggt ccgaaacgat cgggattttt ttttaaaatc ccgatcgttt c        51

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methylguanine
<220> FEATURE:
<221> NAME/KEY: modified_base
<222> LOCATION: (2)..(2)
<223> OTHER INFORMATION: 2'-O-methylcytosine
<220> FEATURE:
<221> NAME/KEY: modified_base
<222> LOCATION: (3)..(3)
<223> OTHER INFORMATION: 2'-O-methylthymine
<220> FEATURE:
<221> NAME/KEY: modified_base
<222> LOCATION: (4)..(4)
<223> OTHER INFORMATION: 2'-O-methylguanine
<220> FEATURE:
<221> NAME/KEY: modified_base
<222> LOCATION: (5)..(5)
<223> OTHER INFORMATION: 2'-O-methylthymine
<220> FEATURE:
<221> NAME/KEY: modified_base
<222> LOCATION: (6)..(6)
<223> OTHER INFORMATION: 2'-O-methylcytosine
<220> FEATURE:
<221> NAME/KEY: modified_base
<222> LOCATION: (7)..(7)
<223> OTHER INFORMATION: 2'-O-methylthymine
<220> FEATURE:
<221> NAME/KEY: modified_base
<222> LOCATION: (8)..(9)
<223> OTHER INFORMATION: 2'-O-methylguanine
<220> FEATURE:
<221> NAME/KEY: modified_base
<222> LOCATION: (10)..(10)
<223> OTHER INFORMATION: 2'-O-methylthymine
<220> FEATURE:
<221> NAME/KEY: modified_base
<222> LOCATION: (11)..(12)
<223> OTHER INFORMATION: 2'-O-methylcytosine
<220> FEATURE:
<221> NAME/KEY: modified_base
<222> LOCATION: (13)..(13)
<223> OTHER INFORMATION: 2'-O-methylguanine
<220> FEATURE:
<221> NAME/KEY: modified_base
<222> LOCATION: (14)..(16)
<223> OTHER INFORMATION: 2'-O-methyladenine
<220> FEATURE:
<221> NAME/KEY: modified_base
<222> LOCATION: (17)..(17)
<223> OTHER INFORMATION: 2'-O-methylcytosine
<220> FEATURE:

```
<221> NAME/KEY: modified_base
<222> LOCATION: (18)..(18)
<223> OTHER INFORMATION: 2'-O-methylguanine
<220> FEATURE:
<221> NAME/KEY: modified_base
<222> LOCATION: (19)..(19)
<223> OTHER INFORMATION: 2'-O-methyladenine
<220> FEATURE:
<221> NAME/KEY: modified_base
<222> LOCATION: (20)..(20)
<223> OTHER INFORMATION: 2'-O-methylthymine
<220> FEATURE:
<221> NAME/KEY: modified_base
<222> LOCATION: (21)..(21)
<223> OTHER INFORMATION: 2'-O-methylcytosine
<220> FEATURE:
<221> NAME/KEY: modified_base
<222> LOCATION: (22)..(24)
<223> OTHER INFORMATION: 2'-O-methylguanine
<220> FEATURE:
<221> NAME/KEY: modified_base
<222> LOCATION: (25)..(25)
<223> OTHER INFORMATION: 2'-O-methyladenine
<220> FEATURE:
<221> NAME/KEY: modified_base
<222> LOCATION: (26)..(30)
<223> OTHER INFORMATION: 2'-O-methylthymine
<220> FEATURE:
<221> NAME/KEY: modified_base
<222> LOCATION: (51)..(51)
<223> OTHER INFORMATION: dideoxy-c

<400> SEQUENCE: 9
gctgtctggt ccgaaacgat cgggattttt ttttaaaatc ccgatcgttt c      51

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: iso-c

<400> SEQUENCE: 10
tnagagtctg gtgccgactc gacgttttcg tcgagtcg                     38

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: dideoxy-c

<400> SEQUENCE: 11
gctgtctggt ccgtcagttt tctgac                                  26

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (32)..(32)
<223> OTHER INFORMATION: dideoxy-c

<400> SEQUENCE: 12
gctgtctggt ccgcgtcacg ttttcgtgac gc                                        32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dideoxy-c

<400> SEQUENCE: 13
gctgtctggt ccgttattat ttttataata ac                                        32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: dideoxy-c

<400> SEQUENCE: 14
gctgtctggt ccgttattac ttttgtaata ac                                        32

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: dideoxy-c

<400> SEQUENCE: 15
gctgtctggt ccgtcatgtt ttcatgac                                             28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: dideoxy-c

<400> SEQUENCE: 16
gctgtctggt ccgtcatatt tttatgac                                             28

<210> SEQ ID NO 17
<211> LENGTH: 36
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(36)
<223> OTHER INFORMATION: dideoxy-c

<400> SEQUENCE: 17
gctgtctggt ccgttattat atttttatat aataac                                 36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(36)
<223> OTHER INFORMATION: dideoxy-c

<400> SEQUENCE: 18
gctgtctggt ccgttattat actttttgtat aataac                                36

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: iso-c
<220> FEATURE:
<221> NAME/KEY: modified_base
<222> LOCATION: (20)..(20)
<223> OTHER INFORMATION: iso-g

<400> SEQUENCE: 19
cacgacaggc agacaggann gctcacgttt tcgtgagct                              39

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: iso-c

<400> SEQUENCE: 20
cacacaggag cannagctca cgttttcgtg agct                                   34

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: iso-c
```

```
<400> SEQUENCE: 21
gctgtctggt nngctcacgt tttcgtgagc                                      30

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: iso-c

<400> SEQUENCE: 22
gctgtctggt nncgctcacg ttttcgtgag cg                                   32

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gctgtctggt cccgctcacg ttttcgtgag cgtt                                 34

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: iso-c

<400> SEQUENCE: 24
gctgtctggt nncgactcga cgttttcgtc gagtcg                               36

<210> SEQ ID NO 25
<211> LENGTH: 36
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(34)
<223> OTHER INFORMATION: 2'-O-methyluracil
<220> FEATURE:
<221> NAME/KEY: modified_base
<222> LOCATION: (35)..(35)
<223> OTHER INFORMATION: 2'-O-methylcytosine
<220> FEATURE:
<221> NAME/KEY: modified_base
<222> LOCATION: (36)..(36)
<223> OTHER INFORMATION: dideoxy-c

<400> SEQUENCE: 25
gctgtctggt ccggactcga cgttttcgtc gagucc                               36
```

```
<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: O-methyl modified

<400> SEQUENCE: 26
gctgtctggt ccgttattat ac                                                  22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: dideoxy-c

<400> SEQUENCE: 27
gctgtctggt ccgttattat ac                                                  22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gctgtctggt ccgttattat ac                                                  22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: dideoxy-c

<400> SEQUENCE: 29
gctgtctggt ataataacgg ac                                                  22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(23)
<223> OTHER INFORMATION: dideoxy-c

<400> SEQUENCE: 30
gctgtctggt ataataacgg acc                                                 23

<210> SEQ ID NO 31
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iso-g
<220> FEATURE:
<221> NAME/KEY: modified_base
<222> LOCATION: (12)..(12)
<223> OTHER INFORMATION: iso-c
<220> FEATURE:
<221> NAME/KEY: modified_base
<222> LOCATION: (17)..(17)
<223> OTHER INFORMATION: iso-g

<400> SEQUENCE: 31
gctgtntggt gngttantat ac                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iso-g
<220> FEATURE:
<221> NAME/KEY: modified_base
<222> LOCATION: (12)..(12)
<223> OTHER INFORMATION: iso-c
<220> FEATURE:
<221> NAME/KEY: modified_base
<222> LOCATION: (17)..(17)
<223> OTHER INFORMATION: iso-g

<400> SEQUENCE: 32
gctgtntggt gngttantat ac                                              22

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iso-c
<220> FEATURE:
<221> NAME/KEY: modified_base
<222> LOCATION: (11)..(11)
<223> OTHER INFORMATION: iso-g
<220> FEATURE:
<221> NAME/KEY: modified_base
<222> LOCATION: (12)..(12)
<223> OTHER INFORMATION: dideoxy-c

<400> SEQUENCE: 33
gtatantaac nc                                                         12

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
```

```
                   oligonucleotide
<220> FEATURE:
<221> NAME/KEY: modified_base
<222> LOCATION: (6)..(6)
<223> OTHER INFORMATION: iso-c
<220> FEATURE:
<221> NAME/KEY: modified_base
<222> LOCATION: (11)..(11)
<223> OTHER INFORMATION: iso-g
<220> FEATURE:
<221> NAME/KEY: modified_base
<222> LOCATION: (14)..(14)
<223> OTHER INFORMATION: dideoxy-c

<400> SEQUENCE: 34
gtatantaac ncac                                                   14

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iso-c
<220> FEATURE:
<221> NAME/KEY: modified_base
<222> LOCATION: (11)..(11)
<223> OTHER INFORMATION: iso-g
<220> FEATURE:
<221> NAME/KEY: modified_base
<222> LOCATION: (15)..(15)
<223> OTHER INFORMATION: dideoxy-c

<400> SEQUENCE: 35
gtatantaac ncacc                                                  15

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iso-g
<220> FEATURE:
<221> NAME/KEY: modified_base
<222> LOCATION: (12)..(12)
<223> OTHER INFORMATION: iso-c
<220> FEATURE:
<221> NAME/KEY: modified_base
<222> LOCATION: (17)..(17)
<223> OTHER INFORMATION: iso-g

<400> SEQUENCE: 36
gctgtntggt angttantat ac                                          22

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iso-c
```

```
-continued

<220> FEATURE:
<221> NAME/KEY: modified_base
<222> LOCATION: (11)..(11)
<223> OTHER INFORMATION: iso-g
<220> FEATURE:
<221> NAME/KEY: modified_base
<222> LOCATION: (14)..(14)
<223> OTHER INFORMATION: dideoxy-c

<400> SEQUENCE: 37
gtatantaac ntac                                                        14
```